United States Patent [19]

Komatsu et al.

[11] Patent Number: 5,637,716
[45] Date of Patent: Jun. 10, 1997

[54] PROCESSES FOR THE PREPARATION OF HYDROQUINONE AND BENZOQUINONE DERIVATIVES

[75] Inventors: Yuuki Komatsu; Norio Minami; Ken Furukawa; Hiroshi Nishimura; Yoji Yamagishi, all of Ibaraki, Japan

[73] Assignees: Eisai Co., Ltd., Tokyo; Eisai Chemical Co., Ltd., Ibaraki, both of Japan

[21] Appl. No.: 578,695

[22] PCT Filed: Jul. 26, 1994

[86] PCT No.: PCT/JP94/01230

§ 371 Date: Dec. 27, 1995

§ 102(e) Date: Dec. 27, 1995

[87] PCT Pub. No.: WO95/04044

PCT Pub. Date: Feb. 9, 1995

[30] Foreign Application Priority Data

| Jul. 30, 1993 | [JP] | Japan | 5-206809 |
| Aug. 31, 1993 | [JP] | Japan | 5-237193 |
| Jul. 18, 1994 | [JP] | Japan | 6-165482 |

[51] Int. Cl.$^6$ .................................. C07D 213/30
[52] U.S. Cl. .................. 546/301; 546/343; 546/340
[58] Field of Search ....................... 546/301, 343, 546/340

[56] References Cited

U.S. PATENT DOCUMENTS

| 4,043,790 | 8/1977 | Krumkalns | 504/155 |
| 4,111,945 | 9/1978 | Jarque et al. | 546/343 |
| 5,541,331 | 7/1996 | Murugan et al. | 546/343 |

FOREIGN PATENT DOCUMENTS 5-148183  6/1993  Japan .

OTHER PUBLICATIONS

Summerford et al "The Hydrolysis of Some Quinone Oxines" vol. 66—pp. 1330–1331 (1994).
Shimizu et al—1992 The Chemical Society of Japan vol. 65, No. 6—pp. 1522–1526 (1992).

*Primary Examiner*—C. Warren Ivy
*Assistant Examiner*—Lyman H. Smith
*Attorney, Agent, or Firm*—Birch, Stewart, Kolasch & Birch

[57] ABSTRACT

Intermediates for the preparation of benzothiazole derivatives useful for the prevention and treatment of diseases for which an inhibitory action against the production of leukotriene and thromboxane is efficacious, and industrially advantageous processes for the preparation of the intermediates. A hydroquinone derivative is condensed with a pyridylcarboxyaldehyde derivative without the protecting the hydroxyl groups of the hydroquinone derivative to form a pyridylmethylhydroquinone derivative, which is further oxidized into a pyridylmethyl-1,4-benzoquinone derivative:

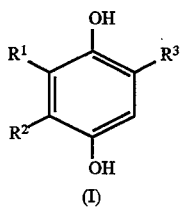

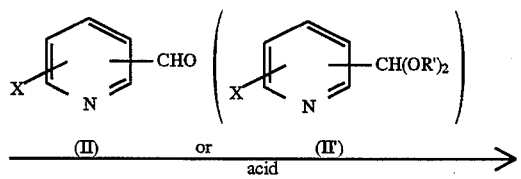

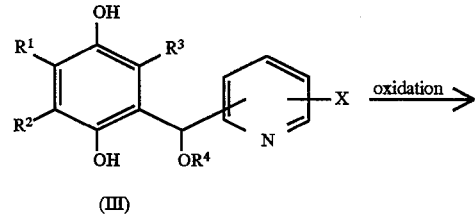

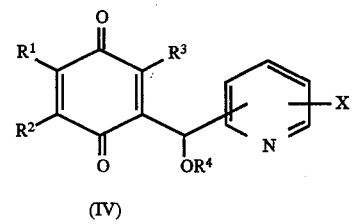

10 Claims, No Drawings

PROCESSES FOR THE PREPARATION OF HYDROQUINONE AND BENZOQUINONE DERIVATIVES

This application is a #35 U.S.C. 371 National Stage filing of PCT/JP94/01230 published as WO 95/04044 on Feb. 9, 1995.

INDUSTRIAL FIELD OF APPLICATION

The present invention relates to processes for the preparation of important intermediates for the synthesis of the benzothiazole derivatives which are disclosed in EP-A 507318 and are useful for the prevention and treatment of diseases for which an inhibitory action against the production of leukotriene and thromboxane is efficacious.

PRIOR ART

The above European Patent (EP-A 507318) also discloses a process for the preparation of a compound (VI) similar to pyridynylmethyl-1,4-benzoquinone derivatives represented by the general formula (IV). This process is, as represented by the following reaction formula (wherein $R^5$ and $R^6$ represent the same or different from each other a hydrogen atom, a lower alkyl group or a lower alkoxy group; and $R^7$ represents a lower alkyl group), one which comprises introducing a pyridylmethanol group into a dimethoxybenzene derivative as a starting material and oxidizing the resulting product with diammonium cerium (IV) nitrate:

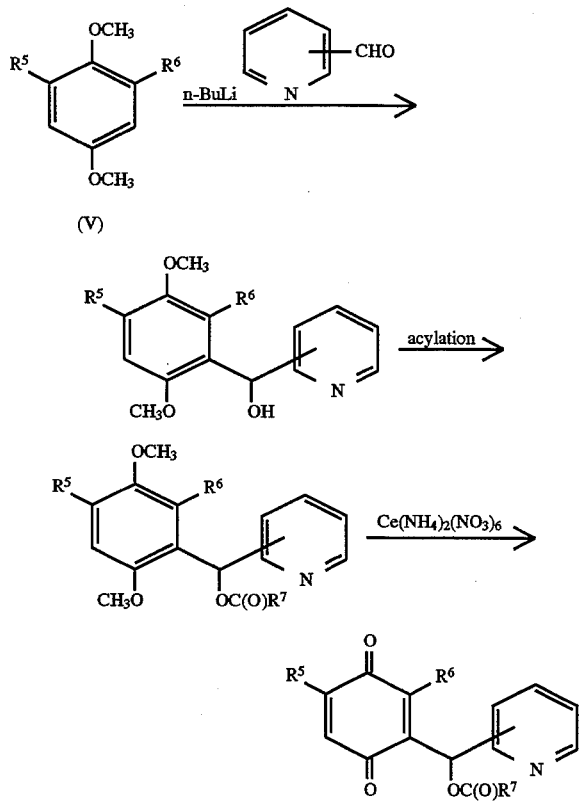

The 2,5-dimethoxybenzene derivative used as the starting material in the process of the prior art is one prepared by methylating a hydroquinone derivative as represented by the following reaction formula (wherein $R^5$ and $R^6$ are each as defined above) for the purpose of protecting the hydroxyl groups of the hydroquinone derivative from the influence of the reagent (i.e., n-BuLi) used in the subsequent introduction of a pyridylmethanol group. However, this methylation is an entirely useless step and industrially disadvantageous, because the methyl groups (introduced as the protecting groups) are removed by oxidation in the oxidation step conducted after the introduction of a pyridiylmethanol group for preparing an objective 1,4-benzoquinone derivative. Further, the oxidation conditions of the methoxy derivative (with the protected hydroxyl groups) are restricted more severely than those of the hydroxy derivative, because the methoxy derivative is more resistant to oxidation than the hydroxy derivative. Thus, the methoxy derivative is disadvantageous also in this respect. Under these circumstances, it has been expected to establish an industrial process for introducing a pyridylmethanol group into a hydroquinone derivative without the necessity for protecting the hydroxyl groups of the derivative and uncostly conditions of the oxidation subsequent to the introduction.

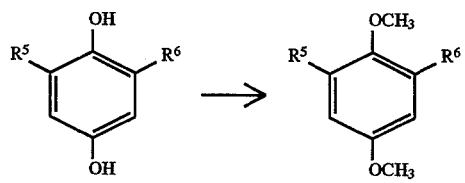

DISCLOSURE OF THE INVENTION

The inventors of the present invention have made intensive studies on the introduction of a pyridylmethyl group into a hydroquinone derivative represented by the general formula (I) without the necessity for protecting the hydroxyl groups of the derivative. As a result of the studies, they have found a process for the preparation of a pyridylmethylhydroquinone derivative represented by the general formula (III) which comprises reacting a hydroquinone derivative represented by the general formula (I) with a pyridinecarboxaldehyde represented by the general formula (II) or an alkyl acetal derivative represented by the general formula (II') in the presence of an acid without the necessity for protecting the hydroxyl groups of the hydroquinone derivative. Further, they have also established a process for preparing a pyridylmethyl-1,4-benzoquinone derivative (IV) through oxidation under inexpensive conditions. Thus, the present invention has been accomplished.

The present invention will now be described in detail.

(1) Step of introduction of pyridylmethyl group

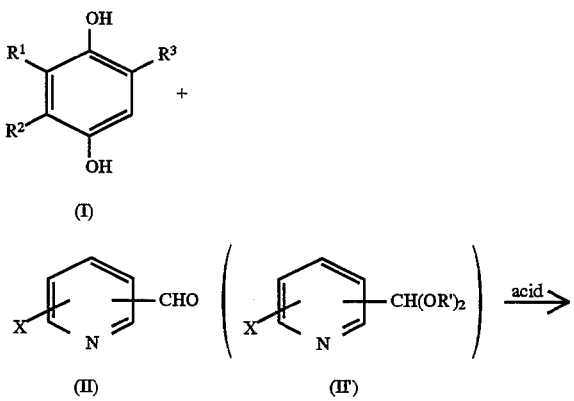

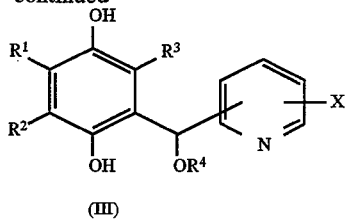

(III)

(wherein $R^1$ represents a hydrogen atom, a methyl group or a methoxy group; $R^2$ and $R^3$ represent the same or different from each other a hydrogen atom or a methyl group; $R^4$ represents a hydrogen atom or a lower alkyl group; $R'$ represents a lower alkyl group; and X represents a hydrogen atom, a lower alkyl group, a lower alkoxy group or a halogen atom).

In this step, a pyridylmethyl derivative (III) is prepared by condensing a hydroquinone derivative (I) with a pyridinecarboxaldehyde derivative (II) or an acetal thereof (II') in the presence of an acid. Examples of the acid include hydrochloric acid, sulfuric acid, phosphoric acid, trifluoroacetic acid and methanesulfonic acid. Examples of the solvent to be used in the above condensation include water, methanol, ethanol, propanol, isopropanol, methylene chloride, 1,2-dichloroethane, benzene, and toluene.

The reaction temperature may range from −10° to 100° C., preferably room temperature to 100° C., still preferably 10° to 30° C. When an acetal derivative (II') is used in the above condensation, a hydroquinone derivative (I) can be also directly added to the reaction mixture given by the reaction of a pyridinecarboxaldehyde derivative (II) with a lower alkyl alcohol without the isolation of the formed acetal to thereby obtain a pyridylalkoxymethyl-1,4-hydroquinone derivative (III).

The hydroquinone derivative used as the starting material (I) can be easily prepared by reducing a 1,4-benzoquinone derivative either with a mild reducing agent such as sodium hydrosulfite, acid sodium sulfite or sodium borohydride by a conventional method or in the presence of platinum oxide or palladium-carbon, the 1,4-benzoquinone derivative being prepared by the process described in J. Am. Chem. Soc., 66, 1330 (1944) or that described in Bull. Chem. Soc. Jpn., 65, 1522 (1992).

(2) Step of oxidation of hydroquinone into benzoquinone

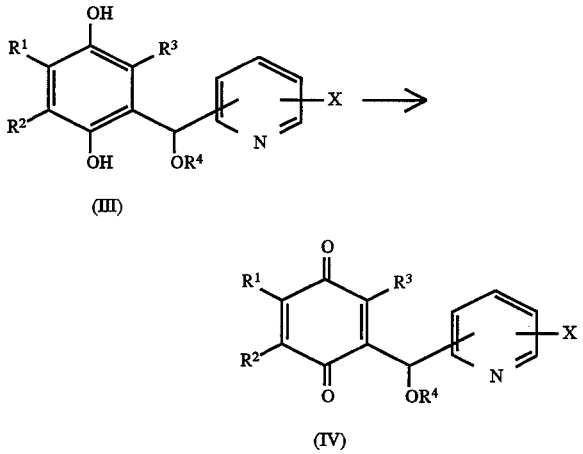

(wherein $R^1$ represents a hydrogen atom, a methyl group or a methoxy group; $R^2$ and $R^3$ represent the same or different from each other a hydrogen atom or a methyl group; $R^4$ represents a hydrogen atom or a lower alkyl group; and X represents a hydrogen atom, a lower alkyl group, a lower alkoxy group or a halogen atom).

In this step, a hydroquinone derivative (III) is oxidized into a 1,4-benzoquinone derivative (IV). Even a mild oxidizing agent can be used in this oxidation. Examples of the oxidizing agent usable in the oxidation include air, oxygen, Fremy' salt, ferric chloride, ferric sulfate, hydrogen peroxide, peracids, silver oxide, diammonium cerium(IV) nitrate, and nitric acid. The above oxidation is generally conducted in the presence of a solvent and examples of the solvent include methanol, acetonitrile, tetrahydrofuran, dioxane, ethyl acetate, 1,2-dimethoxyethane, acetic acid; hydrous solvents comprising these organic solvents and water; and water. The reaction temperature may range from −10° to 100° C., preferably from −10° to 30° C., while the reaction time may range from one minute to three days, generally preferably two hours or shorter.

In the above general formulae (III) and (IV), the lower alkyl as defined with respect to $R^4$ and X may be a linear or branched alkyl group having 1 to 4 carbon atoms. Example thereof include methyl, ethyl, n-propyl, isopropyl, n-butyl, isobutyl and s-butyl, among which methyl, ethyl, n-propyl and isopropyl are preferable. Further, the lower alkoxy as defined with respect to X includes methoxy, ethoxy, n-propoxy, isopropoxy and n-butoxy, while the halogen as defined with respect thereto includes a fluorine atom, a chlorine atom and a bromine atom.

As described above, the present invention relates to an industrially extremely advantageous process. Namely, the present invention enables the direct introduction of a pyridylmethyl group into a hydroquinone derivative without the necessity for blocking the hydroxyl groups of the derivative with a protecting group such as methyl. By virtue of this advantage of the present invention, the oxidation of the pyridylmethylated derivative into a corresponding benzoquinone derivative can be conducted even under mild conditions, which makes it possible to select inexpensive conditions for the oxidation.

The quinone compound (IV) prepared by the process of the present invention can be converted into a 2-amino-6-hydroxy-4-[pyridyl(hydroxy or alkoxy)methyl]benzothiazole derivative (VII) by reacting it with a thiourea represented by the formula: $H_2N—C(=S)—NR^{15}R^{16}$ (wherein $R^{15}$ and $R^{16}$ represent the same or different from each other a hydrogen atom, a lower alkyl group or a pyridylalkyl group) through the reaction disclosed in EP-A 507318.

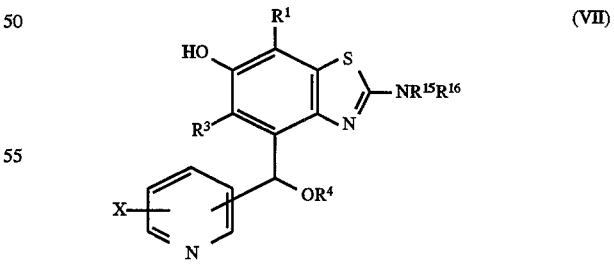

Further, the above derivative (VII) can be reduced into a 2-amino-6-hydroxy-4-pyridylmethylbenzothiazole derivative through the reductive elimination of $R^4O$ by treating the derivative (VII) with zinc in acetic acid under heating. The derivative thus prepared is, as disclosed in EP-A 507318, particularly in Example 10, useful for the prevention and treatment of diseases for which an inhibitory action against the production of leukotriene and thromboxane due to 5-lipoxygenase-inhibiting action and thromboxane production inhibiting action is efficacious and ulcerative colitis.

EXAMPLE

Examples of the present invention will now be described, though it is needless to say that the present invention is not limited by them.

EXAMPLE 1

3.5-Dimethyl -2-(hydroxy-3-pyridylmethyl)benzene-1,4-diol

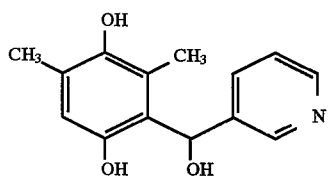

3-Pyridinecarboxyaldehyde (14 ml, 0.15 mol) was dropped into 250 ml of 6N hydrochloric acid under cooling with ice, followed by the addition of 25 g (0.18 mol) of 2,6-dimethyl-p-hydroquinone. The obtained mixture was stirred at room temperature for 17 hours, followed by the addition of 300 ml of water and 25 ml of ethyl acetate. Sodium hydrogencarbonate (111 g, 1.32 mol) was added to the resulting mixture in portions under cooling with ice and vigorous stirring. The obtained mixture was stirred for 10 minutes to precipitate crystals, which were recovered by filtration, washed with water, ethyl acetate and isopropyl ether successively, and dried to give 33.0 g of the title compound (yield: 91%).

M.p.: 181°–183° C. Elemental analysis as $C_{14}H_{15}NO_3$ calcd. C, 68.56; H, 6.16; N, 5.71 found C, 68.32; H, 6.19; N, 5.45 $^1$H-NMR(400 MHz, DMSO-$d_6$) δ: 1.91(3H, s), 2.07 (3H, s), 6.28(1H, s), 6.45(1H, s), 7.27(1H, dd, J=4.0, 8.0 Hz), 7.57(1H, d, J=8.0 Hz), 8.36(1H, d, J=4.0 Hz), 8.42(1H, s). MS(FAB): m/z246 (M+H)$^+$.

EXAMPLE 2

3,5-Dimethyl-2-(methoxy-3-pyridylmethyl)benzene-1,4-diol hydrochloride

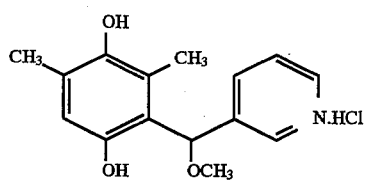

Hydrogen chloride gas was introduced into a solution of 1.0 ml (10.6 mmol) of 3-pyridinecarboxyaldehyde in 15 ml of methanol under cooling with ice for 50 minutes, followed by the addition of 1.6 g (11.6 mmol) of 2,6-dimethyl-p-hydroquinone. The obtained mixture was stirred under cooling with ice for one hour and distilled under a reduced pressure to remove the methanol. Water and ethyl acetate were added to the residue, followed by the neutralization with sodium hydrogencarbonate. The organic phase thus formed was recovered, dried over magnesium sulfate, and distilled under a reduced pressure to remove the solvent. The obtained residue was purified by silica gel column chromatography (ethyl acetate/n-hexane (1:1)) to give 1.8 g of free 3,5-dimethyl-2-(methoxy-3-pyridylmethyl)benzene-1,4-diol. This product was dissolved in a mixture comprising water and 36 ml of ethyl acetate, followed by the dropwise addition of 2.1 ml of 4N hydrogen chloride/ethyl acetate under cooling with ice. The obtained mixture was stirred for 10 minutes to precipitate crystals, which were recovered by filtration, washed with ethyl acetate and isopropyl ether successively, and dried to give 1.8 g of the title compound (yield: 58%).

M.p.: 177°–178° C. Elemental analysis as $C_{15}H_{17}NO_3$·HCl calcd. C, 60.91; H, 6.13; N, 4.74 found C, 60.54; H, 6.13; N, 4.73 $^1$H-NMR(400 MHz, DMSO-$d_6$) δ: 1.88(3H, s), 2.09(3H, s), 3.29(3H, s), 6.14(1H, s), 6.56(1H, s), 7.90(1H, dd, J=5.6, 8.0 Hz), 8.14(1H, d, J=8.0 Hz), 8.59(1H, s), 8.75(1H, d, J=5.6 Hz), 9.10(1H, br s). MS(FAB): m/z260(M+H)$^+$.

EXAMPLE 3

3,5-Dimethyl-2-(hydroxy-4-pyridylmethyl)benzene-1,4-diol

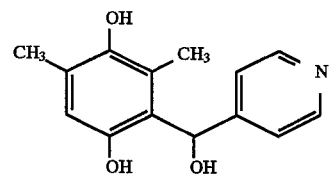

4-Pyridinecarboxyaldehyde (1.0 ml, 10.5 mmol) was dropped into 8 ml of 6N hydrochloric acid under cooling with ice, followed by the addition of 1.59 g (11.5 mmol) of 2,6-dimethyl-p-hydroquinone. The obtained mixture was stirred at room temperature for 17 hours, followed by the addition of 30 ml of water and 20 ml of ethyl acetate. Sodium hydrogencarbonate was added to the resulting mixture in portions under cooling with ice and vigorous stirring to adjust the pH to 6.5. The resulting mixture was left standing to cause phase separation. The ethyl acetate phase thus formed was recovered, dried over magnesium sulfate, and distilled under a reduced pressure to remove the solvent. Ethyl acetate (50 ml) was added to the residue and the obtained mixture was stirred for one hour under cooling with ice to precipitate crystals, which were recovered by filtration, washed with ethyl acetate and isopropyl ether successively, and dried to give 2.02 g of the title compound (yield: 79%).

M.p.: 158°–159° C. Elemental analysis as $C_{14}H_{15}NO_3$ calcd. C, 68.56; H, 6.16; N, 5.71 found C, 68.52; H, 6.17; N, 5.66 $^1$H-NMR(400 MHz, DMSO-$d_6$) δ: 1.88(3H, s), 2.06 (3H, s), 5.98(1H, br s), 6.25(1H, s), 6.45(1H, s) 7.20(2H, d, J=6.0 Hz), 7.38(1H, br s), 8.41(1H, d, J=6.0 Hz). MS(FAB): m/z246(M+H)$^+$.

EXAMPLE 4

3,5-Dimethyl-2-(hydroxy-2-pyridylmethyl)benzene-1,4-diol

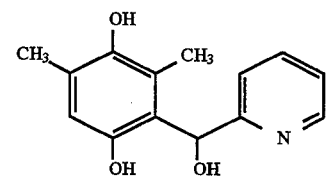

The same procedure as that of Example 1 was repeated except that 1.0 ml (10.5 mmol) of 2-pyridinecarboxyaldehyde was used instead of the 3-pyridinecarboxyaldehyde to give 2.00 g of the title compound (yield: 78%).

M.p.: 160°–161° C. Elemental analysis as $C_{14}H_{15}NO_3$ calcd. C, 68.56; H, 6.16; N, 5.71 found C, 68.57; H, 6.14; N, 5.72 $^1$H-NMR(400 MHz, DMSO-d$_6$) δ: 1.96(3H, s), 2.04 (3H, s), 6.1–6.2(1H, br s), 6.13(1H, s), 6.37(1H. s), 7.19(1H, dd, J=4.8, 8.0 Hz), 7.35(1H, br s), 7.48(1H, d, J=8.0 Hz), 7.73(1H, ddd, J=1.8, 4.8, 8.0 Hz), 8.41(1H, dd, J=1.8, 4.8 Hz), 8.9–9.0(1H, br s). MS(FAB): m/z245(M)$^+$.

EXAMPLE 5

3,5-Dimethyl-2-(isopropyloxy-3-pyridylmethyl) benzene-1,4-diol hydrochloride

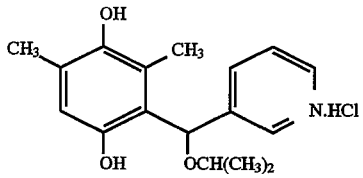

Hydrogen chloride gas was introduced into a solution of 10 g (93.4 mmol) of 3-pyridinecarboxyaldehyde in 100 ml of isopropyl alcohol under cooling with ice for 50 minutes. The resulting solution was distilled under a reduced pressure to remove the solvent. Water and ethyl acetate were added to the residue, followed by the neutralization with sodium hydrogencarbonate. The resulting mixture was left standing to cause phase separation. The ethyl acetate phase thus formed was recovered, dried over magnesium sulfate, and distilled under a reduced pressure to remove the solvent. The obtained residue was purified by silica gel column chromatography (ethyl acetate/dichloromethane (1:3)) to give 3.44 g of 3-pyridinecarboxyaldehyde diisopropyl acetal (yield: 18%).

$^1$H-NMR(400 MHz, CDCl$_3$) δ: 1.18(6H, d, J=6.0 Hz), 1.21(6H, d, J=6.0 Hz), 3.93(2H, qq, J=6.0, 6.0 Hz), 5.60(1H, s), 7.29(1H, dd, J=4.8, 8.0 Hz), 7.81(1H, d, J=8.0 Hz), 8.57(1H, d, J=4.8 Hz), 8.69(1H, s).

Concentrated sulfuric acid (1.77 ml) was dropped into a solution of 3.40 g (16.2 mmol) of the above 3-pyridinecarboxyaldehyde diisopropyl acetal in 45 ml of isopropyl alcohol, followed by the addition of 3.07 g (22.2 mmol) of 2,6-dimethyl-p-hydroquinone. The obtained mixture was stirred at room temperature for 17 hours and distilled under a reduced pressure to remove the isopropyl alcohol. Water and ethyl acetate were added to the residue, followed by the neutralization with sodium hydrogencarbonate. The organic phase thus formed was recovered, dried over magnesium sulfate, and distilled under a reduced pressure to remove the solvent. The obtained residue was purified by silica gel column chromatography (ethyl acetate/n-hexane (2:1))) to give 2.7 g of free 3,5-dimethyl-2-(isopropyloxy-3-pyridylmethyl)-benzene-1,4-diol (yield: 58%). This product (1.0 g) was dissolved in 15 ml of ethyl acetate, followed by the dropwise addition of 1.1 ml of 4N hydrogen chloride/ethyl acetate under cooling with ice. The resulting mixture was stirred for 10 minutes to precipitate crystals, which were recovered by filtration and dissolved in 30 ml of acetonitrile under heating. The resulting solution was allowed to stand at room temperature for 3 hours. The crystals thus precipitated were recovered by filtration and dried to give 0.78 g of the title compound.

M.p.: 171°–173° C. (dec.) Elemental analysis as $C_{17}H_{21}NO_3 \cdot$HCl calcd. C, 63.06; H, 6.85; N, 4.33 found C, 62.96; H, 6.74; N, 4.34 $^1$H-NMR(400 MHz, DMSO-d$_6$) δ: 1.09(3H, d, J=6.0 Hz), 1.21(3H, d, J=6.0 Hz), 1.85(3H, s), 2.09(3H, s), 3.62(1H, qq, J=6.0, 6.0 Hz), 6.36(1H, s), 6.57(1H, s), 7.93(1H, dd, J=5.6, 8.0 Hz), 8.15(1H, d, 8.55 (1H, s), 8.77(1H, d, J=5.6 Hz). MS(FAB): m/z288(M+H)$^+$.

EXAMPLE 6

2-(Hydroxy-3-pyridylmethyl)-5-methylbenzene-1,4-diol

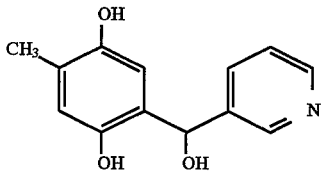

A solution of 1.0 ml (11.8 mmol) of 3-pyridinecarboxyaldehyde in 3 ml of tetrahydrofuran was dropped into 12 ml of 5N hydrochloric acid under cooling with ice, followed by the addition of 1.46 g (11.8 ml) of 2-methyl-p-hydroquinone. The obtained mixture was stirred at room temperature for 3 days, neutralized with sodium hydrogencarbonate, and extracted with ethyl acetate. The ethylacetate phase was washed with water, dried, and distilled under a reduced pressure to remove the solvent. The obtained residue was purified by silica gel column chromatography (ethyl acetate/dichloromethane (1:1)) to give 0.45 g of the title compound (yield: 18%).

M.p.: 175°–176° C. (dec.) $^1$H-NMR(400 MHz, DMSO-d$_6$) δ: 1.98(3H, s), 5.90(1H, s), 6.45(1H, s), 6.79(1H, s), 6.84(1H, br s), 7.27(1H, dd, J=4.8, 8.0 Hz), 7.61(1H, d, J=8.0 Hz), 8.35(1H, d, J=4.8 Hz), 8.4–8.5(1H, br s), 8.50 (1H, s), 8.66(1H, s). MS(FAB): m/z232(M+H)$^+$.

EXAMPLE 7

2-(Hydroxy-3-pyridylmethyl)benzene-1,4-diol

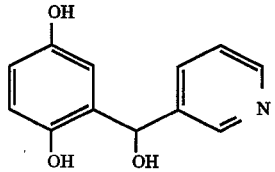

The same procedure as that of Example 1 was repeated except that 1.95 g (17.7 mmol, 1.5 eq. based on the aldehyde) of p-hydroquinone was used instead of the 2,6-dimethyl-p-hydroquinone and that the reaction was conducted at room temperature for 43 hours, followed by the purification by column chromatography (ethyl acetate/dichloromethane (1:1)). The title compound (0.80 g) was obtained as an amorphous substance (yield: 35%).

$^1$H-NMR(400 MHz, DMSO-d$_6$) δ: 5.75–5.85(1H, br s), 5.91(1H, s), 6.42(1H, dd, J=2.8, 8.4 Hz), 6.55(1H, d, J=8.4 Hz), 6.82(1H, d, J=2.8 Hz), 7.27(1H, dd, J=4.8, 8.0 Hz), 7.64(1H, d, J=8.0 Hz), 8.36(1H, d, J=4.8 Hz), 8.51(1H, s), 8.6–8.7(1H, br s), 8.75–8.85(1H, br s). MS(FAB): m/z218 (M+H)$^+$.

EXAMPLE 8

3,5-Dimethyl-2-(ethoxy-3-pyridylmethyl)benzene-1,4-diol hydrochloride

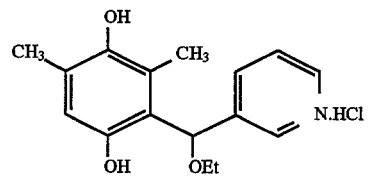

2,6-Dimethyl-p-hydroquinone (2.5 g, 18.1 mmol) was added to 25 ml of a solution of 1.6 ml (16.5 mmol) of 3-pyridinecarboxyaldehyde in 20% (w/w) hydrochloric acid/ethanol. The obtained mixture was stirred at room temperature for 23 hours and distilled under a reduced pressure to remove the ethanol. Water and ethyl acetate were added to the residue, followed by the neutralization with sodium hydrogencarbonate. The organic phase thus formed was recovered, dried over magnesium sulfate, and distilled under a reduced pressure to remove the solvent. The residue was purified by silica gel column chromatography (ethyl acetate/n-hexane (1:1)) to give 3.2 g of free 3,5-dimethyl-2-(ethoxy-3-pyridylmethyl)benzene-1,4-diol (yield: 71%). This product (1.7 g) was dissolved in 33 ml of ethyl acetate, followed by the dropwise addition of 1.8 ml of 4N hydrogen chloride/ethyl acetate under cooling with ice. The obtained mixture was stirred for 10 minutes to precipitate crystals, which were recovered by filtration, followed by the addition of 60 ml of acetonitrile. The obtained mixture was heated under reflux for 10 minutes and stirred at room temperature for one hour to give a precipitate, which was recovered by filtration, washed with acetonitrile and isopropyl ether successively, and dried to give 1.1 g of the title compound.

M.p.: 185°–187° C. (dec.) Elemental analysis as $C_{16}H_{19}NO_3 \cdot HCl$ calcd. C, 62.03; H, 6.51; N, 4.52 found C, 61.96; H, 6.59; N, 4.56 $^1$H-NMR(400 MHz, DMSO-$d_6$) δ: 1.18(3H, t, J=6.8), 1.88(3H, s), 2.08(3H, s), 3.47(3H, m), 6.24(1H, s), 6.56(1H, s), 7.93(1H, dd, J=5.6, 8.0 Hz), 8.17(1H, d, J=8.0 Hz), 8.58(1H, s), 8.76(1H, d, J=5.6 Hz). MS(FAB): m/z274(M+H)$^+$.

EXAMPLE 9

3.5-Dimethyl-2-(hydroxy-6-methylpyridylmethyl)-benzene-1,4-diol

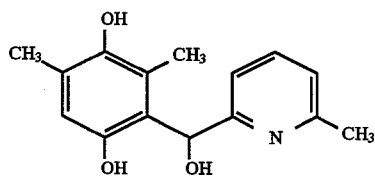

The same procedure as that of Example 1 was repeated except that 6-methyl-2-pyridinecarboxyaldehyde was used instead of the 3-pyridinecarboxyaldehyde. The title compound was obtained in a yield of 88%.

M.p.: 176°–178° C. (dec.) Elemental analysis as $C_{15}H_{17}NO_3 \cdot 0.36H_2O$ calcd. C,67.78; H, 6.72; N, 5.27 found C, 67.77; H, 6.70; N, 5.22 $^1$H-NMR(400 MHz, DMSO-$d_6$) δ: 2.00(3H, s), 2.05(3H, s), 2.45(3H, s), 6.10(1H, s), 6.2(1H, br s), 6.38(1H, s), 7.18(1H, br s), 7.22(1H, d, J=8.0 Hz), 7.41(1H, s), 7.7(1H, br s). MS(FAB): m/z 259(m+H)$^+$

EXAMPLE 10

3.5-Dimethyl-2-(hydroxy-4-chloropyridylmethyl)benzene-1,4-diol

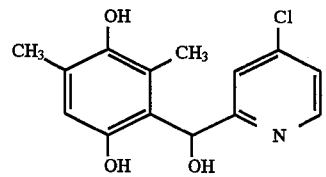

The same procedure as that of Example 1 was repeated except that 6-chloro-2-pyridinecarboxyaldehyde was used instead of the 3-pyridinecarboxyaldehyde. The title compound was obtained in a yield of 89%.

M.p.: 155°–187° C. (dec.) Elemental analysis as $C_{14}H_{14}NO_3Cl$ calcd. C, 60.11; H, 5.04; N, 5.01 found C, 59.94; H, 5.16; N, 5.03 $^1$H-NMR(400 MHz, DMSO-$d_6$) δ: 1.95(3H, s), 2.04(3H, s), 6.1(2H, b), 6.36(1H, s), 7.33(1H, dd, J=2.0, 5.2 Hz), 7.37(1H, s), 7.61(1H, d, J=2.0 Hz), 8.36(1H, d, J=5.2 Hz), 8.75(1H, s). MS(FAB): m/z279(M)$^+$.

EXAMPLE 11

2-(hydroxy-3-pyridylmethyl)-3,5,6-trimethylbenzene-1,4-diol

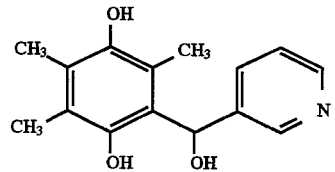

The same procedure as that of Example 1 was repeated except that 2,3,5-trimethyl-p-hydroquinone was used instead of the 2,6-dimethyl-p-hydroquinone. The title compound was obtained in a yield of 86%.

M.p.: 206°–207° C. (dec.) Elemental analysis as $C_{15}H_{17}NO_3$ calcd. C, 69.48; H, 6.61; N, 5.40 found C, 69.43; H, 6.64; N, 5.35 $^1$H-NMR(400 MHz, DMSO-$d_6$) δ: 1.98(3H, s), 2.02(3 H, s), 2.06(3H, s), 6.18(1H, s), 7.1(1H, s), 7.31(1H, dd, J=4.8, 8.0 Hz), 7.4(1H, br s), 7.59(1H, d, J=8.0 Hz), 8.41(1H, d, J=4.8 Hz), 8.46(1H, s), 8.9(1H, br s). MS(FAB): m/z260(M+H)$^+$.

EXAMPLE 12

3,5-Dimethyl-2-(hydroxy-3-pyridylmethyl)-1,4-benzoquinone hydrochloride

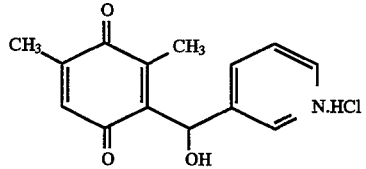

3,5-Dimethyl-2-(hydroxy-3-pyridylmethyl)benzene-1,4-diol (30 g, 0.12 mol) was dissolved in a solution comprising 60 ml of water and 60 ml of tetrahydrofuran. Concentrated nitric acid (78 ml) was dropped into the obtained solution under cooling with ice and stirring in 15 minutes. After 5 minutes, 450 ml of ethyl acetate and 60 ml of water were added to the obtained mixture and the resulting mixture was neutralized by the addition of a solution of 64 g of sodium carbonate in 250 ml of water and 17.3 g of sodium hydrogencarbonate. The resulting mixture was left standing to cause phase separation. The ethyl acetate phase thus formed was recovered, washed with water and a saturated aqueous solution of common salt, and dried over magnesium sulfate. After the removal of the magnesium sulfate, 88.7 ml of 4N hydrogen chloride/ethyl acetate was dropped into the resulting ethyl acetate solution under cooling with ice. The obtained mixture was stirred for 15 minutes to precipitate crystals, which were recovered by filtration, washed with ethyl acetate and isopropyl ether, and dried to give 30.4 g of the title compound (yield: 90%).

M.p.: 155°–180° C. (dec.) $^1$H-NMR(400 MHz, DMSO-$d_6$) δ: 1.97(3H, d, J=1.6 Hz), 1.98(3H, s), 6.14(1H, s), 6.68(1H, d, J=1.6 Hz), 7.95(1H, dd, J=5.6, 8.0 Hz), 8.40(1H, d, J=8.0 Hz), 8.76(1H, s), 8.77(1H, d, J=5.6 Hz). MS(FAB): m/z244($M^+$+H).

EXAMPLE 13

3,5-Dimethyl-2-(methoxy-3-pyridylmethyl)-1,4-benzoquinone

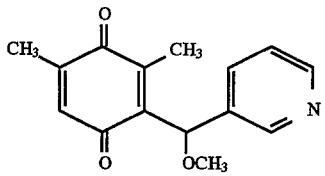

3,5-Dimethyl-2-(methoxy-3-Pyridylmethyl) benzene-1,4-diol hydrochloride (1.0 g, 3.38 mmol) was dissolved in a mixture comprising 3 ml of water and 2 ml of tetrahydrofuran. Concentrated nitric acid (3 ml) was dropped into the obtained solution under cooling with ice in 5 minutes. After 5 minutes, 15 ml of ethyl acetate and 2 ml of water were added to the obtained mixture, followed by the neutralization with sodium carbonate and a saturated aqueous solution of sodium hydrogencarbonate. The resulting mixture was left standing to cause phase separation. The ethyl acetate phase thus formed was recovered, washed with water and a saturated aqueous solution of common salt, dried over magnesium sulfate, and distilled under a reduced pressure to give 1.0 g of the title compound as an oil (yield: 100%).

$^1$H-NMR(400 MHz, CDCl$_3$) δ: 2.07(3H, d, J=1.6 Hz), 2.10(3H, s), 3.42(3H, s), 5.90(1H, s), 6.63(1H, d, J=1.6 Hz), 7.26(1H, dd, J=4.8, 8.0 Hz), 7.68(1H, d, J=8.0 Hz), 8.50(1H, d, J=4.8 Hz), 8.56(1H, s).

EXAMPLE 14

3,5-Dimethyl-2-(isopropyloxy-3-pyridylmethyl)-1,4-benzoquinone hydrochloride

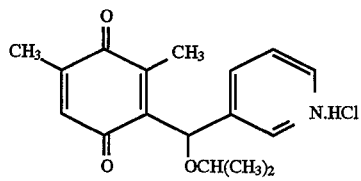

3,5-Dimethyl-2-(isopropyloxy-3-pyridylmethyl)-benzene-1,4-diol (2.3 g, 8.01 mmol) was dissolved in 34.5 ml of ethyl acetate, followed by the addition of a solution of 4.33 g (16.03 mmol) of ferric chloride hexahydrate (FeCl$_3$·6H$_2$O) in 10 ml of water. The obtained mixture was vigorously stirred for 2 minutes. After the completion of the reaction, 3.37 g (40.1 mmol) of sodium hydrogencarbonate was added to the resulting mixture under cooling with ice. The obtained mixture was filtered through Celite to remove insolubles. The filtrate was extracted with ethyl acetate, and the ethyl acetate phase was washed with water and a saturated aqueous solution of common salt and dried over magnesium sulfate. After the removal of the magnesium sulfate, 9.6 ml of 4N hydrogen chloride/ethyl acetate was dropped into the resulting ethyl acetate solution. The resulting mixture was distilled under a reduced pressure to remove the solvent, giving 2.3 g of the title compound (yield: 89%).

$^1$H-NMR(400 MHz, CDCl$_3$) δ: 1.20(3H, d, J=6.0 Hz), 1.24(3H, d, J=6.0 Hz), 2.00(3H, s), 2.09(3H, d, J=1.6 Hz), 3.72(1H, qq, J=6.0, 6.0 Hz), 6.21(1H, s), 6.67(1H, d, J=1.6 Hz), 7.87(1H, dd, J=5.6, 8.0 Hz), 8.30(1H, d, J=8.0 Hz), 8.67(1H, d, J=5.6 Hz), 8.77(1H, s).

EXAMPLE 15

3,5-Dimethyl-2-hydroxy-3-pyridylmethyl)-1,4-benzoquinone hydrochloride 3,5-Dimethyl-2-(hydroxy-3-pyridylmethyl) benzene-1,4-diol (0.5 g, 2.04 mmol) was dissolved in a solution comprising 1.0 ml of water and 3.0 ml of methanol, followed by the addition of 17 mg of cupric chloride dihydrate (CuCl$_2$·2H$_2$O). The obtained mixture was stirred for 1.5 hours while air was bubbled into the mixture. Ethyl acetate (15 ml) and water (10 ml) were added to the resulting mixture and the pH of the obtained mixture was adjusted to 7 with a saturated aqueous solution of sodium hydrogencarbonate. The resulting mixture was left standing to cause phase separation. The ethyl acetate phase thus formed was recovered, washed with water and a saturated aqueous solution of common salt, and dried over magnesium sulfate. After the removal of the magnesium sulfate, 0.56 ml of 4N hydrogen chloride/ethyl acetate was dropped into the resulting ethyl acetate solution under cooling with ice. The obtained mixture was stirred for 15 minutes to precipitate crystals, which were recovered by filtration, washed with ethyl acetate and isopropyl ether, and dried to give 0.46 g of the title compound (yield: 81%). The melting point and $^1$H-NMR spectrum of this product agreed with those of the compound of Example 12.

There will now be described Application Examples wherein 2-amino-6-hydroxy-4-pyridylmethylbenzothiazole compounds useful as drugs are prepared from the quinone compounds prepared according to the present invention.

APPLICATION EXAMPLE 1

[4-(6-Hydroxy-5,7-dimethyl-2-methylamino) benzothiazoyl]-(3-pyridyl)methanol

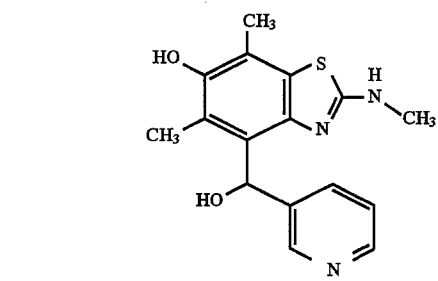

Concentrated hydrochloric acid (21.7 ml) was added to a suspension of 30 g (0.11 mol) of [2-(3,5-dimethyl-1,4- benzoquinonyl)]-(3-pyridyl)methanol hydrochloride (2) in 300 ml of ethanol under cooling with ice, followed by the addition of 9.68 g (0.11 mol) of methylthiourea. The obtained mixture was solution at 4° C. for 15 hours (whereby the reaction solution became dissolved and was thereafter increased in the amount of precipitates). Ethyl acetate (300 ml) was added to the resulting mixture. The obtained mixture was stirred for 10 minutes and filtered to recover a precipitate, which was washed with ethyl acetate and isopropyl ether to give a corresponding thiouronium salt. This salt was suspended in 300 ml of ethanol, followed by the addition of a solution of 2.9 g of 1,4-benzoquinone in 23.8 ml of tetrahydrofuran under cooling with ice. The obtained mixture was stirred at 4° C. for 4 hours and then at 20° C. for 3 hours, followed by the addition of 200 ml of ethyl acetate. The obtained mixture was stirred for 10 minutes and filtered to recover precipitates, which were washed with ethyl acetate and isopropyl ether and dried to give 36.3 g (93.8 mol) of hydrochloride of the title compound. This hydrochloride was dissolved in 524 ml of water, followed by the addition of 145 ml of ethyl acetate. Sodium hydrogencarbonate (17.3 g, 0.21 mol) was added to the obtained mixture under cooling with ice. The precipitates thus formed were recovered by filtration, washed with ethyl acetate and isopropyl ether, and dried in the presence of phosphorus pentaoxide to give 26.9 g (85.5 mol) of the title compound (yield: 79.9%).

M.p.: 201°–203° C. (dec.) $^1$H-NMR(400 MHz, DMSO-$d_6$) δ: 2.03(3H, s), 2.21(3H, s), 2.88(3H, d, J=4.8 Hz), 6.51(1H, d, J=6.6 Hz), 6.55(1H, d, J=6.6 Hz), 7.27(1H, dd, J=4.8, 8 Hz), 7.60(1H, d, J=8 Hz), 7.82(1H, d, J=4.8 Hz), 7.97(1H, s), 8.35(1H, d, J=4.8 Hz), 8.46(1H, s). MS(FAB): m/z316(M+H)$^+$.

APPLICATION EXAMPLE 2

6-Hydroxy-5,7-dimethyl-2-methylamino-4-(3-pyridylmethyl) benzothiazole

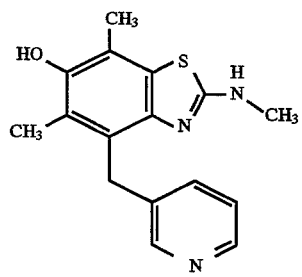

Zinc powder (2.6 g, 39.8 mmol) was added to a solution of 5.0 g (15.9 mmol) of [4-(6-hydroxy-5,7-dimethyl-2-methylamino) benzothiazolyl]-(3-pyridyl)methanol (3) in 50 ml of acetic acid. The obtained mixture was heated under reflux for 26 hours and filtered in a hot state to remove insolubles. Ethyl acetate (200 ml) was added to the filtrate, followed by the stirring under cooling with ice for 10 minutes.

The precipitate thus Formed was recovered by filtration and dissolved in 100 ml of ethanol, Followed by the dropwise addition of 24 ml of 4N hydrochloric acid/ethyl acetate under cooling with ice. The obtained mixture was stirred For 30 minutes.

The precipitate thus Formed was recovered by Filtration, washed with ethyl acetate and isopropyl ether, and dried to give 5.9 g of hydrochloride of the title compound. This hydrochloride was dissolved 100 ml of water, followed by the addition of 75 ml of ethyl acetate. The resulting mixture was neutralized with a saturated aqueous solution of sodium hydrogencarbonate under cooling with ice to form a precipitate, which was recovered by Filtration and suspended in 75 ml of ethanol. The obtained suspension was heated under reflux for one hour, stirred under cooling with ice for 15 minutes and filtered. The precipitate thus recovered was washed with ethanol and dried to give 2.9 g (9.69 mmol) of the title compound (yield: 60.9%).

M.p.: 220°–223° C. (dec.) $^1$H-NMR(400 MHz, DMSO-$d_6$) δ: 2.07(3H, s), 2.20(3H, s), 2.87(3H, d, J=4.8 Hz), 4.25(2H, s), 7.20(1H, dd, J=4.7, 8 Hz), 7.48(1H, d, J=8 Hz), 7.65(1H, d, J=4.8 Hz), 7.90(1H, br), 8.31(1H, d), 8.44(1H, s).

We claim:

1. A process for the preparation of a hydroquinone derivative represented by the following general formula (III):

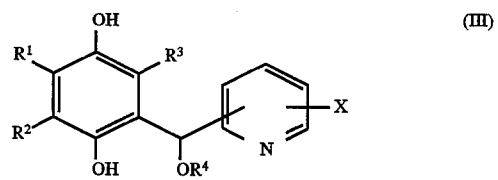

(wherein $R^1$ represents a hydrogen atom, a methyl group or a methoxy group; $R^2$ and $R^3$ represent the same or different from each other a hydrogen atom or a methyl group; $R^4$ represents a hydrogen atom or a lower alkyl group; and X represents a hydrogen atom, a lower alkyl group, a lower alkoxy group or a halogen atom) or a salt thereof, which characterized by condensing a hydroquinone derivative represented by the following general formula (I):

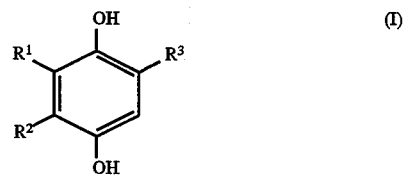

(wherein $R^1$ represents a hydrogen atom, a methyl group or a methoxy group; and $R^2$ and $R^3$ represent the same or different from each other a hydrogen atom or a methyl group) with an aldehyde derivative represented by the following general formula (II) or (II'):

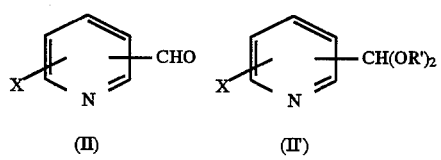

(wherein X represents a hydrogen atom, a lower alkyl group, a lower alkoxy group or a halogen atom; and R' represents a lower alkyl group) in the presence of an acid.

2. A process for the preparation of a 1,4-benzoquinone derivative represented by the following general formula (IV):

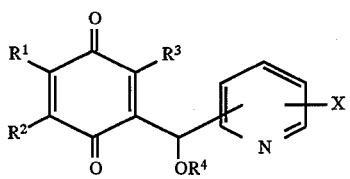

(wherein $R^1$ represents a hydrogen atom, a methyl group or a methoxy group; $R^2$ add $R^3$ represent the same or different from each other a hydrogen atom or a methyl group; $R^4$ represents a hydrogen atom or a lower alkyl group; and X represents a hydrogen atom, a lower alkyl group, a lower alkoxy group or a halogen atom) or a salt thereof, which characterized by oxidizing a hydroquinone derivative represented by the following general formula (III):

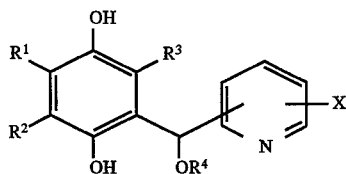

(wherein $R^1$ represents a hydrogen atom, a methyl group or a methoxy group; $R^2$ and $R^3$ represent the same or different from each other a hydrogen atom or a methyl group; $R^4$ represents a hydrogen atom or a lower alkyl group; and X represents a hydrogen atom, a lower alkyl group, a lower alkoxy group or a halogen atom).

3. A process for the preparation of a hydroquinone derivative or a salt thereof as set forth in claim 1, wherein $R^1$ and $R^3$ represent the same or different from each other a hydrogen atom or a methyl group; and $R^2$ and X each represent a hydrogen atom in the following general formula (III).

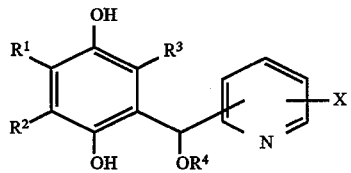

4. A process for the preparation of a 1,4-benzoquinone derivative or a salt thereof as set forth in claim 2, wherein $R^1$ and $R^3$ represent the same or different from each other a hydrogen atom or a methyl group; and $R^2$ and X each represent a hydrogen atom in the following general formula (IV):

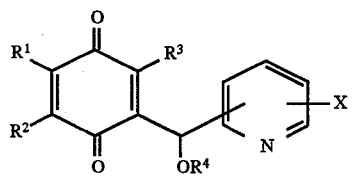

5. A hydroquinone derivative represented by the following general formula (III) or a salt thereof as set forth in claim 1:

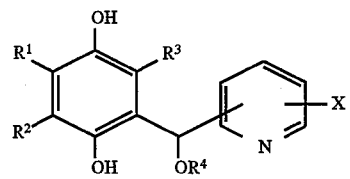

(wherein $R^1$ represents a hydrogen atom, a methyl group or a methoxy group; $R^2$ and $R^3$ represent the same or different from each other a hydrogen atom or a methyl group; $R^4$ represents a hydrogen atom or a lower alkyl group; and X represents a hydrogen atom, a lower alkyl group, a lower alkoxy group or a halogen atom).

6. A 1,4-benzoquinone derivative represented by the following general formula (IV) or a salt thereof as set forth in claim 2:

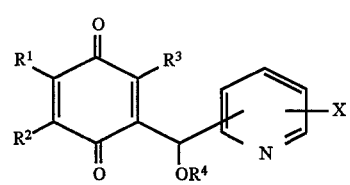

(wherein $R^1$ represents a hydrogen atom, a methyl group or a methoxy group; $R^2$ and $R^3$ represent the same or different from each other a hydrogen atom or a methyl group; $R^4$ represents a hydrogen atom or a lower alkyl group; and X represents a hydrogen atom, a lower alkyl group, a lower alkoxy group or a halogen atom).

7. A hydroquinone derivative represented by the following general formula (III) or a salt thereof as set forth in claim 1:

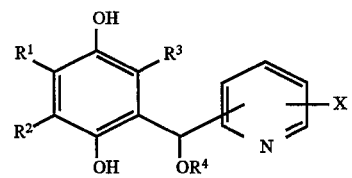

wherein $R^1$ and $R^3$ each represent a methyl group; and $R^2$ and X each represent a hydrogen atom.

8. A 1,4-benzoquinone derivative represented by the following general formula (IV) or a salt thereof as set forth in claim 2:

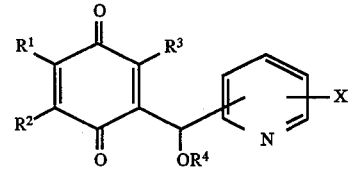

wherein $R^1$ and $R^3$ each represent a methyl group; and $R^2$ and X each represent a hydrogen atom.

9. A process for the preparation of a 1,4-benzoquinone derivative represented by the general formula (IV) or a salt thereof which characterized by condensing a hydroquinone derivative represented by the general formula (I) with an aldehyde derivative represented by the general formula (II) or (II') in the presence of an acid to form a hydroquinone derivative represented by the general formula (III) and oxidizing this hydroquinone derivative or a salt thereof:

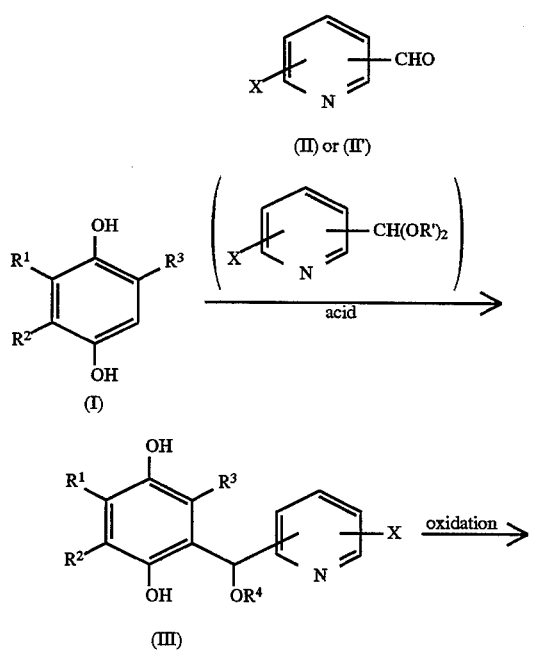

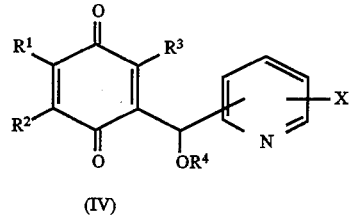

(wherein $R^1$ represents a hydrogen atom, a methyl group or a methoxy group; $R^2$ and $R^3$ represent the same or different from each other a hydrogen atom or a methyl group; R' represents a lower alkyl group; $R^4$ represents a hydrogen atom or a lower alkyl group; and X represents a hydrogen atom, a lower alkyl group, a lower alkoxy group or a halogen atom).

10. A process for the preparation of 3,5-dimethyl-2-(hydroxy-3-pyridylmethyl)-1,4-benzoquinone or a salt thereof which characterized by condensing 3-pyridinecarboxyaldehyde with 2,6-dimethyl-p-hydroquinone in the presence of an acid to form 3,5-dimethyl-2-(hydroxy-3-pyridylmethyl)-benzene-1,4-diol and oxidizing the diol.

* * * * *